(12) United States Patent
Snow et al.

(10) Patent No.: US 8,758,221 B2
(45) Date of Patent: Jun. 24, 2014

(54) SOURCE RESERVOIR WITH POTENTIAL ENERGY FOR REMOTELY ADJUSTABLE GASTRIC BANDING SYSTEM

(75) Inventors: Sean Snow, Carpinteria, CA (US); Mike Augarten, Goleta, CA (US); Christian Perron, Goleta, CA (US); Joseph Raven, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 264 days.

(21) Appl. No.: 12/711,876

(22) Filed: Feb. 24, 2010

(65) Prior Publication Data

US 2011/0208229 A1    Aug. 25, 2011

(51) Int. Cl.
*A61M 29/00* (2006.01)
*A61B 17/08* (2006.01)
*A61F 5/00* (2006.01)
*A61F 2/04* (2013.01)

(52) U.S. Cl.
CPC ............. *A61F 5/0056* (2013.01); *A61F 5/0059* (2013.01); *A61F 2250/0001* (2013.01); *A61F 2/04* (2013.01); *A61F 5/0053* (2013.01); *A61F 5/0043* (2013.01); *A61F 5/0046* (2013.01); *A61F 5/0036* (2013.01); *A61F 2002/045* (2013.01)
USPC .............................. 600/37; 606/192; 606/157

(58) Field of Classification Search
CPC ................ A61F 5/0056; A61F 5/0059; A61F 2250/0001; A61F 2/04; A61F 5/0053; A61F 5/0043; A61F 5/0046; A61F 5/0036; A61F 2002/045

USPC ............... 128/897–99; 600/29–32, 37; 604/9; 606/157, 192
See application file for complete search history.

(56) References Cited

U.S. PATENT DOCUMENTS

| | | | |
|---|---|---|---|
| 1,174,814 A | | 3/1916 | Brennan et al. |
| 1,830,947 A | | 11/1931 | Klingel |
| 1,999,683 A | | 4/1935 | Borresen |
| 2,112,106 A | * | 3/1938 | Longstreet ................ 137/228 |
| 2,163,048 A | | 6/1939 | McKee |
| 2,339,138 A | | 1/1944 | Black |
| 2,405,667 A | | 8/1946 | Ottesen |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.

(Continued)

*Primary Examiner* — Christine Matthews
*Assistant Examiner* — Joshua D Lannu
(74) *Attorney, Agent, or Firm* — Gordon & Jacobson, PC

(57) ABSTRACT

The present invention includes a source reservoir with potential energy for a system for facilitating obesity control. The system includes a remote transmitter, a gastric band including at least one inflatable portion for containing a fluid, at least one reservoir for containing the fluid, and a high precision pump unit in communication with the reservoir for controlling pressure within the inflatable portion.

12 Claims, 5 Drawing Sheets

(56) References Cited

U.S. PATENT DOCUMENTS

| | | |
|---|---|---|
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchick |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak |
| 4,592,355 A | 6/1986 | Antebi |
| 4,601,713 A | 7/1986 | Fuqua |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki |
| 4,886,787 A | 12/1989 | De Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,089,019 A | 2/1992 | Grandjean |
| 5,091,171 A | 2/1992 | Yu et al. |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A * | 10/1995 | Racchini et al. ............... 604/19 |
| 5,496,312 A | 3/1996 | Klicek |
| 5,509,888 A | 4/1996 | Miller |
| 5,531,716 A | 7/1996 | Luzio et al. |
| 5,535,752 A | 7/1996 | Halperin |
| 5,554,113 A | 9/1996 | Novak |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | ANG.gerup |
| 5,653,718 A | 8/1997 | Yoon |
| 5,658,298 A | 8/1997 | Vincent et al. |
| 5,676,162 A | 10/1997 | Larson, Jr. |
| 5,695,504 A | 12/1997 | Gifford, III et al. |
| 5,704,893 A | 1/1998 | Timm |
| 5,713,911 A | 2/1998 | Racenet et al. |
| 5,733,257 A * | 3/1998 | Sternby ............................ 604/27 |
| 5,748,200 A | 5/1998 | Funahashi |
| 5,759,015 A | 6/1998 | Van Lintel et al. |
| 5,766,232 A | 6/1998 | Grevious |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador |
| 6,042,345 A | 3/2000 | Bishop et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,164,933 A | 12/2000 | Tani et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,387,105 B1 | 5/2002 | Gifford, III et al. |
| 6,417,750 B1 | 7/2002 | Sohn |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyas Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |

(56) References Cited

U.S. PATENT DOCUMENTS

| | | | |
|---|---|---|---|
| 6,470,892 | B1 | 10/2002 | Forsell |
| 6,474,584 | B2 | 11/2002 | Ekich |
| 6,475,136 | B1 | 11/2002 | Forsell |
| 6,485,496 | B1 | 11/2002 | Suyker et al. |
| 6,491,704 | B2 | 12/2002 | Gifford, III et al. |
| 6,491,705 | B2 | 12/2002 | Gifford, III et al. |
| 6,511,490 | B2 | 1/2003 | Robert |
| 6,517,556 | B1 | 2/2003 | Monassevitch |
| 6,527,701 | B1 | 3/2003 | Sayet et al. |
| 6,547,801 | B1 | 4/2003 | Dargent et al. |
| 6,565,582 | B2 | 5/2003 | Gifford, III et al. |
| 6,579,301 | B1 | 6/2003 | Bales et al. |
| 6,601,604 | B1 | 8/2003 | Cooper |
| 6,615,084 | B1 | 9/2003 | Cigaina |
| 6,632,239 | B2 | 10/2003 | Snyder et al. |
| 6,646,628 | B2 | 11/2003 | Shirochi et al. |
| 6,676,674 | B1 | 1/2004 | Dudai |
| 6,681,135 | B1 | 1/2004 | Davis et al. |
| 6,685,668 | B1 | 2/2004 | Cho et al. |
| 6,691,047 | B1 | 2/2004 | Fredericks |
| 6,715,731 | B1 | 4/2004 | Post et al. |
| 6,729,600 | B2 | 5/2004 | Mattes et al. |
| 6,754,527 | B2 | 6/2004 | Stroebel |
| 6,811,136 | B2 | 11/2004 | Eberhardt et al. |
| 6,820,651 | B2 | 11/2004 | Seuret et al. |
| 6,834,201 | B2 | 12/2004 | Gillies |
| 6,871,090 | B1 | 3/2005 | He |
| 6,889,086 | B2 | 5/2005 | Mass et al. |
| 6,916,326 | B2 | 7/2005 | Benchetrit |
| 6,940,467 | B2 | 9/2005 | Fischer |
| 6,966,875 | B1 | 11/2005 | Longobardi |
| 7,017,583 | B2 | 3/2006 | Forsell |
| 7,017,883 | B2 | 3/2006 | Bayer et al. |
| 7,021,147 | B1 | 4/2006 | Subramanian |
| 7,037,344 | B2 | 5/2006 | Kagan et al. |
| 7,040,349 | B2 | 5/2006 | Moler et al. |
| 7,048,519 | B2 | 5/2006 | Fong et al. |
| 7,054,690 | B2 | 5/2006 | Imran |
| 7,058,434 | B2 | 6/2006 | Wang |
| 7,060,080 | B2 | 6/2006 | Bachmann |
| 7,066,486 | B2 | 6/2006 | Lee |
| 7,118,526 | B2 | 10/2006 | Egle |
| 7,119,062 | B1 | 10/2006 | Alvis et al. |
| 7,128,750 | B1 | 10/2006 | Stergiopulos |
| 7,144,400 | B2 | 12/2006 | Byrum et al. |
| 7,172,607 | B2 | 2/2007 | Hofle et al. |
| 7,177,693 | B2 | 2/2007 | Starkebaum |
| 7,191,007 | B2 | 3/2007 | Desai |
| 7,198,250 | B2 | 4/2007 | East |
| 7,204,821 | B1 | 4/2007 | Clare et al. |
| 7,206,637 | B2 | 4/2007 | Salo |
| 7,223,239 | B2 | 5/2007 | Schulze et al. |
| 7,238,191 | B2 | 7/2007 | Bachmann |
| 7,240,607 | B2 | 7/2007 | Fish |
| 7,255,675 | B2 | 8/2007 | Gertner et al. |
| 7,263,405 | B2 | 8/2007 | Boveja et al. |
| 7,282,023 | B2 | 10/2007 | Frering |
| 7,284,966 | B2 | 10/2007 | Xu et al. |
| 7,288,064 | B2 | 10/2007 | Boustani et al. |
| 7,297,103 | B2 | 11/2007 | Jarsaillon et al. |
| 7,299,082 | B2 | 11/2007 | Feldman et al. |
| 7,310,557 | B2 | 12/2007 | Maschino et al. |
| 7,311,503 | B2 | 12/2007 | Van Lintel et al. |
| 7,311,716 | B2 | 12/2007 | Byrum |
| 7,311,717 | B2 | 12/2007 | Egle |
| 7,314,443 | B2 | 1/2008 | Jordan et al. |
| 7,314,636 | B2 | 1/2008 | Caseres et al. |
| 7,338,433 | B2 | 3/2008 | Coe |
| 7,340,306 | B2 | 3/2008 | Barrett et al. |
| 7,351,198 | B2 | 4/2008 | Byrum |
| 7,351,240 | B2 | 4/2008 | Hassler |
| 7,353,747 | B2 | 4/2008 | Swayze et al. |
| 7,364,542 | B2 | 4/2008 | Jambor et al. |
| 7,366,571 | B2 | 4/2008 | Armstrong |
| 7,367,340 | B2 | 5/2008 | Nelson |
| 7,367,937 | B2 | 5/2008 | Jambor |
| 7,374,565 | B2 | 5/2008 | Hassler, Jr. |
| 7,390,294 | B2 | 6/2008 | Hassler |
| 7,396,353 | B2 | 7/2008 | Lorenzen |
| 7,416,528 | B2 | 8/2008 | Crawford et al. |
| 7,457,668 | B2 | 11/2008 | Cancel et al. |
| 7,481,763 | B2 | 1/2009 | Hassler |
| 7,500,944 | B2 | 3/2009 | Byrum |
| 7,502,649 | B2 | 3/2009 | Ben-Haim et al. |
| 7,530,943 | B2 | 5/2009 | Lechner |
| 7,594,885 | B2 | 9/2009 | Byrum |
| 7,599,743 | B2 | 10/2009 | Hassler |
| 7,599,744 | B2 | 10/2009 | Giordano |
| 7,601,162 | B2 | 10/2009 | Hassler, Jr. et al. |
| 7,615,001 | B2 | 11/2009 | Jambor |
| 7,618,365 | B2 | 11/2009 | Jambor |
| 7,658,196 | B2 | 2/2010 | Ferreri |
| 7,670,279 | B2 | 3/2010 | Gertner |
| 7,699,770 | B2 | 4/2010 | Hassler |
| 7,712,470 | B2 | 5/2010 | Gertner |
| 7,727,141 | B2 | 6/2010 | Hassler, Jr. et al. |
| 7,741,476 | B2 | 6/2010 | Lebreton |
| 7,758,493 | B2 | 7/2010 | Gingras |
| 7,763,039 | B2 | 7/2010 | Ortiz et al. |
| 7,766,815 | B2 | 8/2010 | Ortiz |
| 7,771,439 | B2 | 8/2010 | Griffiths |
| 7,775,215 | B2 | 8/2010 | Hassler, Jr. et al. |
| 7,775,966 | B2 | 8/2010 | Dlugos et al. |
| 7,775,967 | B2 | 8/2010 | Gertner |
| 7,794,386 | B2 | 9/2010 | Brooks |
| 7,811,298 | B2 | 10/2010 | Birk |
| 7,828,813 | B2 | 11/2010 | Mouton |
| 7,832,407 | B2 | 11/2010 | Gertner |
| 7,841,978 | B2 | 11/2010 | Gertner |
| 7,844,342 | B2 | 11/2010 | Dlugos et al. |
| 7,862,502 | B2 | 1/2011 | Pool et al. |
| 7,879,068 | B2 | 2/2011 | Dlugos et al. |
| 7,951,067 | B2 | 5/2011 | Byrum et al. |
| 2001/0011543 | A1 | 8/2001 | Forsell |
| 2002/0072780 | A1 | 6/2002 | Foley |
| 2002/0091395 | A1 | 7/2002 | Gabbay |
| 2002/0095181 | A1 | 7/2002 | Beyar |
| 2002/0098097 | A1 | 7/2002 | Singh |
| 2002/0139208 | A1 | 10/2002 | Yatskov |
| 2002/0183765 | A1 | 12/2002 | Adams |
| 2002/0198548 | A1 | 12/2002 | Robert |
| 2003/0014003 | A1 | 1/2003 | Gertner |
| 2003/0019498 | A1 | 1/2003 | Forsell |
| 2003/0045775 | A1 | 3/2003 | Forsell |
| 2003/0045902 | A1 | 3/2003 | Weadock |
| 2003/0055311 | A1 | 3/2003 | Neukermans et al. |
| 2003/0060873 | A1 | 3/2003 | Gertner et al. |
| 2003/0066536 | A1 | 4/2003 | Forsell |
| 2003/0073880 | A1 | 4/2003 | Polsky et al. |
| 2003/0093157 | A1 | 5/2003 | Casares et al. |
| 2003/0100910 | A1 | 5/2003 | Gifford, III et al. |
| 2003/0120288 | A1 | 6/2003 | Benchetrit |
| 2003/0148995 | A1 | 8/2003 | Piron et al. |
| 2003/0158564 | A1 | 8/2003 | Benchetrit |
| 2003/0158569 | A1 | 8/2003 | Wazne |
| 2003/0181890 | A1 | 9/2003 | Schulze et al. |
| 2003/0181917 | A1 | 9/2003 | Gertner |
| 2003/0191433 | A1* | 10/2003 | Prentiss .................... 604/74 |
| 2003/0208212 | A1 | 11/2003 | Cigaina |
| 2004/0000843 | A1 | 1/2004 | East |
| 2004/0044332 | A1 | 3/2004 | Stergiopulos |
| 2004/0049209 | A1 | 3/2004 | Benchetrit |
| 2004/0059393 | A1 | 3/2004 | Policker et al. |
| 2004/0068847 | A1 | 4/2004 | Belisle et al. |
| 2004/0133219 | A1 | 7/2004 | Forsell |
| 2004/0147816 | A1 | 7/2004 | Policker et al. |
| 2004/0148034 | A1 | 7/2004 | Kagan et al. |
| 2004/0153106 | A1 | 8/2004 | Dudai |
| 2004/0162595 | A1 | 8/2004 | Foley |
| 2004/0215159 | A1 | 10/2004 | Forsell |
| 2004/0230137 | A1 | 11/2004 | Mouton |
| 2004/0254536 | A1 | 12/2004 | Conlon et al. |
| 2004/0254537 | A1 | 12/2004 | Conlon et al. |
| 2004/0260319 | A1 | 12/2004 | Egle |

(56) References Cited

U.S. PATENT DOCUMENTS

| | | |
|---|---|---|
| 2004/0267288 A1 | 12/2004 | Byrum |
| 2004/0267291 A1 | 12/2004 | Byrum et al. |
| 2004/0267292 A1 | 12/2004 | Byrum |
| 2004/0267293 A1 | 12/2004 | Byrum et al. |
| 2004/0267377 A1 | 12/2004 | Egle |
| 2005/0002984 A1 | 1/2005 | Byrum |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1* | 11/2005 | Coe ................ 600/31 |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0272968 A1* | 12/2005 | Byrum et al. ............. 600/31 |
| 2005/0277899 A1 | 12/2005 | Conlon et al. |
| 2005/0283041 A1 | 12/2005 | Egle |
| 2005/0288739 A1 | 12/2005 | Hassler |
| 2005/0288740 A1 | 12/2005 | Hassler |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler |
| 2006/0189888 A1 | 8/2006 | Hassler |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1* | 11/2006 | Maschino et al. ............. 607/40 |
| 2006/0252982 A1 | 11/2006 | Hassler et al. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1* | 7/2007 | Birk ............... 600/37 |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0298005 A1 | 12/2007 | Thibault |
| 2008/0009680 A1 | 1/2008 | Hassler |
| 2008/0015406 A1 | 1/2008 | Dlugos |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0166028 A1 | 7/2008 | Turek et al. |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos |
| 2008/0243071 A1 | 10/2008 | Quijano et al. |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |

(56) References Cited

U.S. PATENT DOCUMENTS

| | | | |
|---|---|---|---|
| 2008/0319435 | A1 | 12/2008 | Rioux et al. |
| 2009/0054914 | A1 | 2/2009 | Lechner |
| 2009/0062825 | A1 | 3/2009 | Pool et al. |
| 2009/0062826 | A1 | 3/2009 | Steffen |
| 2009/0082793 | A1 | 3/2009 | Birk |
| 2009/0118572 | A1 | 5/2009 | Lechner |
| 2009/0149874 | A1 | 6/2009 | Ortiz et al. |
| 2009/0157106 | A1 | 6/2009 | Marcotte |
| 2009/0157107 | A1 | 6/2009 | Kierath et al. |
| 2009/0157113 | A1 | 6/2009 | Marcotte et al. |
| 2009/0171375 | A1 | 7/2009 | Coe et al. |
| 2009/0171378 | A1 | 7/2009 | Coe |
| 2009/0171379 | A1 | 7/2009 | Coe et al. |
| 2009/0187202 | A1 | 7/2009 | Ortiz et al. |
| 2009/0192404 | A1 | 7/2009 | Ortiz |
| 2009/0192415 | A1 | 7/2009 | Ortiz et al. |
| 2009/0192533 | A1 | 7/2009 | Dlugos, Jr. et al. |
| 2009/0192534 | A1 | 7/2009 | Ortiz et al. |
| 2009/0192541 | A1 | 7/2009 | Ortiz et al. |
| 2009/0198261 | A1 | 8/2009 | Schweikert |
| 2009/0202387 | A1 | 8/2009 | Dlugos, Jr. et al. |
| 2009/0204131 | A1 | 8/2009 | Ortiz |
| 2009/0204132 | A1 | 8/2009 | Ortiz |
| 2009/0204141 | A1 | 8/2009 | Dlugos, Jr. et al. |
| 2009/0204179 | A1 | 8/2009 | Dlugos, Jr. et al. |
| 2009/0209995 | A1 | 8/2009 | Byrum et al. |
| 2009/0216255 | A1 | 8/2009 | Coe et al. |
| 2009/0220176 | A1 | 9/2009 | Fusco |
| 2009/0222031 | A1 | 9/2009 | Axelsson |
| 2009/0222065 | A1 | 9/2009 | Dlugos, Jr. et al. |
| 2009/0228063 | A1 | 9/2009 | Dlugos, Jr. et al. |
| 2009/0228072 | A1 | 9/2009 | Coe et al. |
| 2009/0270904 | A1 | 10/2009 | Birk et al. |
| 2009/0306462 | A1 | 12/2009 | Lechner |
| 2009/0312785 | A1 | 12/2009 | Stone et al. |
| 2010/0010291 | A1 | 1/2010 | Birk |
| 2010/0087843 | A1 | 4/2010 | Bertolote et al. |
| 2010/0099945 | A1 | 4/2010 | Birk et al. |
| 2010/0100079 | A1 | 4/2010 | Berkcan |
| 2010/0145378 | A1 | 6/2010 | Gertner |
| 2010/0152532 | A1 | 6/2010 | Marcotte |
| 2010/0168508 | A1 | 7/2010 | Gertner |
| 2010/0185049 | A1 | 7/2010 | Birk et al. |
| 2010/0191265 | A1 | 7/2010 | Lau et al. |
| 2010/0191271 | A1 | 7/2010 | Lau et al. |
| 2010/0204647 | A1 | 8/2010 | Gertner |
| 2010/0204723 | A1 | 8/2010 | Gertner |
| 2010/0226988 | A1 | 9/2010 | Lebreton |
| 2010/0228080 | A1 | 9/2010 | Tavori et al. |
| 2010/0234682 | A1 | 9/2010 | Gertner |
| 2010/0249803 | A1 | 9/2010 | Griffiths |
| 2010/0280310 | A1 | 11/2010 | Raven |
| 2010/0305397 | A1 | 12/2010 | Birk et al. |
| 2010/0312147 | A1 | 12/2010 | Gertner |
| 2010/0324358 | A1 | 12/2010 | Birk et al. |
| 2010/0324359 | A1 | 12/2010 | Birk |
| 2011/0201874 | A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09048 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/70131 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |

(56) References Cited

FOREIGN PATENT DOCUMENTS

| | | |
|---|---|---|
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/109300 | 9/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Dixon et al.; "Pregnancy After Lap-Band Surgery: Management of the Band to Achieve Healthy Weight Outcomes"; Obesity Surgery; V. 11, pp. 59-65; 2001.

Helioscopie Product Insert for Heliogast, pp. 1-11 (undated).

Neary et al.; "Peptide YY(3-36) and Glucagon-Like Peptide-$1_{(7-36)}$ Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Patient Management After Lap-Band Placement; http://www.core.monash.org/patient-care.pdf, accessed Mar. 16, 2012.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

The Lap-Band Device & How it Works; http://lapband.com/en/learn_about-lapband/device_how_it_works/, Accessed Mar. 16, 2012.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

"Innovative medical devices and implants"; LGSP medical futures, p. 5.

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

Adrian et al.; "Mechanism of Pancreatic Polypeptide Release in Man." The Lancet; pp. 161-163; Jan. 22, 1977.

Anson; "Shape Memory Alloys—Medical Applications," Source: Materials World, vol. 7, No. 12, pp. 745-747, Dec. 1999.

Asakawa et al; "Antagonism of Ghrelin Receptor Reduces Food Intake and Body Weight Gain in Mice"; Gut.; V.52; pp. 947-952; 2003.

Baggio et al. "Biology of Incretins: GLP-1 and GIP"; Gastroenrology; V. 132; pp. 2131-2157; 2007.

Ballantyne; "Peptide YY(1-36) and Peptide YY(3-36): Part I. Distribution, Release, and Actions"; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; "Physiology"; V. 5; pp. 55-57, 210, 428, 540, 554, 579, 584, 591; 2004.

BioEnterics Corporation, an Inamed Company, BioEnterics Intragastric Balloon; Directions for Use Published Document, P/N 94200 Rev: B, pp. 1-56.

BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; "Can Gut Hormones Control Appetite and Prevent Obesity?" Diabetes Care; V. 31; Supp 2; pp. S284-S289; Feb. 2008.

Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; received Apr. 24, 2004; received in revised form Jul. 12, 2002; 10 pages.

Corno et al.; "FlowWatchTM in clipped and in clipped position"; Interact Cardio Vase Thorac Surg 2002; 1:46-49; Copyright @ 2002 The European Association for Cardio-thoracic Surgery; 1 page.

Cummings et al.; "Plasma Ghrelin Levels After Diet-Induced Weight Loss or Gastric Bypass Surgery"; N. Engl J. Med; V. 346, No. 21; pp. 1623-1630; May 23, 2002.

Cummings; "Gastrointestinal Regulation of Foot Intake"; The Food Journal of Clinical Investigation; V. 117, N. 1; pp. 13-23; Jan. 2007.

Dakin et al.; "Oxyntomodulin Inhibits Food Intake in the Rat"; Endocrinology; V. 142; No. 10; pp. 4244-4250; 2001.

Dakin et al.; "Peripheral Oxyntomodulin Reduces Food Intake and Body Weight gain in Rats"; Endocrinology; V. 145; No. 6; pp. 2687-2695; Jun. 2004.

Davison; "Activation of Vagal-Gastric Mechanoreceptors by Cholecystokinin"; Proc. West. Pharmocol. Soc.; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; "Molecular Weight of Heparin Using 13C Nuclear Magnetic Resonance Spectroscopy" Journal of Pharmaceutical Science, V. 84, I 2; 1995, Abstract only.

Doldi et al.; "Intragastric Balloon: Another Option for Treatment of Obesity and Morbid Obesity"; Hepato-Gastroenterology; V. 51, N. 55; pp. 294-307; Jan.-Feb. 2004.

Doldi et al.; "Treatment of Morbid Obesity with Intragastric Balloon in Association with Diet"; Obesity Surgery; V. 10, pp. 583-587; 2000.

Doldi et al; "Intragastric Balloon in Obese Patients"; Obesity Surgery; V. 10, 578-581; 2000.

Ekblad et al.; "Distribution of Pancreatic Peptide and Peptide-YY"; Peptides; V. 23; pp. 251-261; 2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

(56) References Cited

OTHER PUBLICATIONS

Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Iverson et al.; "Recent Advances in Microscale Pumping Technologies: A Review and Evaluation"; Microfluid Nanofluid; vol. 5; pp. 145-174; Feb. 19, 2008.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V.13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: A Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.
Small et al.; "Gut hormones and the control of appetite"; Trends in Endocrinology and Metabolism; V. 15. No. 6; pp. 259-263; Aug. 2004.
Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptide1 secretion"; J. Physiol.; V.587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.

\* cited by examiner

SOURCE RESERVOIR WITH POTENTIAL ENERGY FOR REMOTELY ADJUSTABLE GASTRIC BANDING SYSTEM

FIELD OF THE INVENTION

The present invention generally relates to medical systems and apparatus and uses thereof for treating obesity and/or obesity-related diseases, and more specifically, relates to a source reservoir with potential energy that is used in a remotely adjustable gastric banding system.

BACKGROUND

Adjustable gastric banding systems provide an effective and substantially less invasive alternative to gastric bypass surgery and other conventional surgical weight loss procedures. Despite the sustained weight loss of invasive weight loss procedures, such as gastric bypass surgery, it has been recognized that sustained weight loss can also be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size to be partially restricted by a gastric band, the tension on the upper portion of the stomach at rest and during food passage provides a feeling of satiety or fullness, thereby facilitating the reduction of the daily caloric intake. Unlike gastric bypass procedures, the gastric band apparatus are reversible and require no permanent modification to the gastrointestinal tract.

Over time, a stoma created by the gastric band may need an adjustment in order to maintain an appropriate size, which is neither too restrictive nor too passive. Accordingly, conventional gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

It would be desirable to allow for non-invasive adjustment of gastric band constriction, for example, without use of the hypodermic needle. Thus, remotely adjustable gastric banding systems have been capable of non-invasive adjustment are described herein.

SUMMARY

In one example embodiment of the invention, there is an implantable device that uses energy to facilitate the movement of fluid to an inflatable portion of a gastric band. The implantable device includes a source reservoir. The source reservoir holds the fluid. The source reservoir has an elastic shell capable of contracting due to a first inward pressure.

The implantable device includes a source valve. The source valve is coupled between the source reservoir and the gastric band. The source valve is open or closed based on a first telemetric signal received from a remote transmitter. When the source valve is open, the first inward pressure causes the elastic shell to contract causing a portion of the fluid in the source reservoir to move into the inflatable portion of the gastric band. When the source valve is closed, the fluid does not move outside the source reservoir.

DETAILED DESCRIPTION

The present invention generally provides remotely adjustable gastric banding systems, for example, for treatment of obesity and obesity related conditions, as well as systems for controlling inflation of a gastric banding system.

Remotely adjustable gastric banding systems, otherwise referred to as a remotely adjustable band (RAB), is one or more medical devices, or a system, which allows a healthcare worker to adjust a gastric band without requiring a hypodermic needle to connect to an implanted access port. The RAB may use a remote transmitter to send radio-frequency signals for powering and communicating with an implanted device of the RAB. The implanted device can fill or drain a gastric band of the RAB as requested by the healthcare worker via the remote transmitter. In between filling and draining adjustments to the gastric band, the volume of fluid contained in the gastric band ideally remains unchanged.

In one embodiment, potential energy is applied on a source reservoir to facilitate movement of the fluid to the gastric band. The source reservoir itself may contain or store the potential energy. Additional potential energy can be provided by an elastic band surrounding the source reservoir. By using potential energy to move the fluid, less electrical energy is needed.

Figure 1:
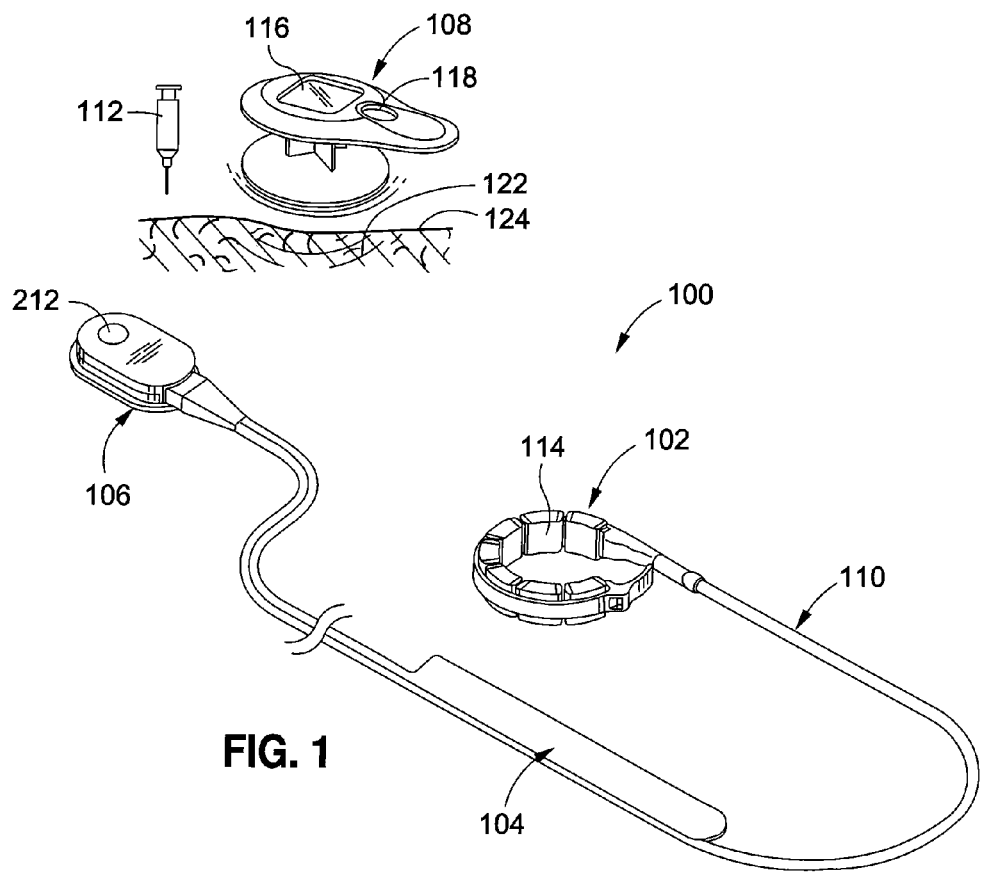
FIG. 1 illustrates an overall schematic view of an example configuration of components according to an embodiment of the present invention.

FIG. 1 illustrates a gastric banding system 100 according to an embodiment of the present invention. The gastric banding system 100 includes a gastric band 102, a reservoir 104, a high precision pump unit 106, a remote transmitter 108 and tubing 110. The skin 124 of a patient illustrates a separation between implantable components and non-implantable components. As illustrated, the remote transmitter 108 (e.g., remote controller unit) is non-implantable, whereas the gastric band 102, the reservoir 104, the high precision pump unit 106, and the tubing 110 are implantable (e.g., an implantable device), and can be implanted in a patient using conventional surgical techniques. The high precision pump unit 106 can be used to replace or complement a conventional access port for adjusting inflation and deflation of the gastric band 102. In some embodiments, the gastric banding system 100 includes an override port 212, which can be used, for example, with a hypodermic needle 112, to fill and drain the gastric band 102.

The high precision pump unit 106 is connected to the reservoir 104 and the gastric band 102 via the tubing 110, and can move precisely metered volumes of fluid (e.g., saline) into or out of the gastric band 102. Moving the fluid into the gastric band 102 causes inflation of at least one bladder, or an inflatable portion 114 (e.g., inflatable member) and constricts around the cardia, or upper portion of the stomach, forming a stoma that restricts the passage of food into a lower portion of the stomach. This stoma can provide a patient with a sensation of satiety or fullness that discourages overeating. In contrast, moving the fluid out of the inflatable portion 114 of the gastric band 102 contracts the pressure around the cardia and allows the stoma to be at least partially released and regains the patient's hunger sensation.

The high precision pump unit 106 is implanted within a patient, and therefore, is non-biodegradable. The encasement of the high precision pump unit 106 is hermetically sealed from the in situ environment (e.g., undisturbed environment) in the patient and formed at least partially of any rugged plastic material including polypropylene, cyclicolephin co-polymer, nylon, and other compatible polymers and the like or at least partially formed of a non-radioopaque metal such as titanium. Other materials may include elastic polymer, rubber, non-rubber, silicon, non-silicon, and combinations thereof. The encasement has a smooth exterior shape, with no jagged edges, to minimize foreign body response and tissue irritation. The high precision pump unit 106 is also sterilizable, for example, dry heat sterilizable before implantation.

The reservoir 104 may be a soft, collapsible balloon made of a biocompatible polymer material, for example, silicone, which holds a reserve of a biocompatible fluid, for example, saline, to allow for adjustments in the size of the gastric band 102. In one embodiment, the reservoir 104 is fully collapsible and can contain the extra fluid needed to increase the volume of the gastric band 102 to therapeutic levels. Further, the reservoir 104 may also have excess capacity so that the gastric band 102 may be fully drained into it without the reservoir 104 being filled beyond its maximum capacity.

The fluids used within the systems of the present invention include any fluid that is biocompatible. The fluid has no adverse effect on the patient in the unlikely event that a leak emanates from the systems. The fluid can simply be water or any biocompatible polymer oil such as castor oil. In an example embodiment, the fluid is saline.

The tubing 110 is any biocompatible flexible tubing that does not degrade in vivo (e.g., within the patient). The tubing 110 is configured to withstand hydraulic pressure up to about 30 psi (about 206 kPa) without leakage. This hydraulic pressure tolerance is true of the entire fluid path of the systems described herein. Although the systems described herein do not generally leak, if they do, fluid is not lost at a rate greater than about 0.2 cc/yr, or about 0.1 cc/yr.

Other biocompatible and biostable polymers which are useful for forming the reservoir 104 and the tubing 110 include polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The systems and apparatus described herein further include the remote transmitter 108 (e.g., a remote controller unit), which provides access to system data and functions, and can be an external, handheld, reusable battery-powered device. The remote transmitter 108 can be made of any rugged plastic material including polypropylene, cyclicolephin co-polymer, nylon, and other compatible polymers and the like. The remote transmitter 108 is not implanted within the patient so hermetic sealing of the unit is not required. However, in one embodiment, the remote transmitter 108 is at least water resistant, if not waterproof, and can be cleaned using standard hospital disinfectants without damage to the unit.

Further, the remote transmitter 108 has a user interface including at least one display 116 and at least one user input 118. In some example embodiments, the display 116 and the user input 118 are combined in the form of a touch screen with a color display. In other embodiments, the display is grayscale. The remote transmitter 108 permits a clinician or a patient to navigate through menu driven screens used for data entry, data collection, and controlling the high precision pump unit 106.

The remote transmitter 108 is capable of communicating with the high precision pump unit 106. "Capable of communicating" as used herein refers to the remote controller's or transmitter's ability to establish communications with the high precision pump unit 106 yet still have the ability to break communication and the systems described herein still function. To establish communication, in one example embodiment, once the remote transmitter 108 is initialized, the display 116 shows a searching query for a nearby high precision pump unit 106. As the remote transmitter 108 is brought into range of the high precision pump unit 106, a symbol displays the strength of the communication link. Once stable communications have been acquired, the display 116 shows the serial number of the system or other unique patient identification code so a clinician can verify they have the appropriate patient records in hand. If the patient requires a tightening of the gastric band 102, the clinician can enter the amount of the desired volume increase. The remote transmitter 108 can also display the current volume within the gastric band 102 and indicate the new volume as the gastric band 102 fills. The display 116 can also indicate the desired and actual volumes during draining of the gastric band 102.

To verify the appropriate adjustment has been made to the system, the clinician can set the remote transmitter 108 into a pressure monitor mode and request that the patient drink water. The display 118 shows a real time graph of the pressure measured within the gastric band 102. This diagnostic tool may show higher pressures and warning messages if the gastric band 102 has been over-tightened.

The remote transmitter 108 can synchronize and charge when coupled to a charging cradle or docking station. The docking station provides the ability to recharge a rechargeable battery of the remote transmitter 108 and provides a link to download information to a personal computer such as the adjustment history of a patient. Other data that can be stored on the remote transmitter 108 and downloaded from the high precision pump unit 106 includes, but is not limited to, serial number, gastric band size, patient information, firmware version and patient adjustment history. This data can be downloaded directly to a patient tracking database for easy tracking.

Any data stored on the remote transmitter 108 or within the high precision pump unit 106 can be electronically secured.

In other words, security measures can be put in place to keep the data confidential, including communication between the high precision pump unit 106 and the remote transmitter 108. The security measures can include computer generated algorithms that prevent intrusion by outside parties.

The reservoir 104 may represent one or both of a source reservoir and a drain reservoir, where the source reservoir provides the fluid to the gastric band 102, and the drain reservoir receives the fluid from the gastric band 102.

The high precision pump unit 106 can contain a microfluidic pump with active valves. In such an embodiment, the high precision pump unit 106 is a passive device that can only be powered by the remote transmitter 108 when it is in close proximity. For example, in one example embodiment, the remote transmitter 108 may be configured to power and communicate with the high precision pump unit 106 at any distance less than about 8 inches, in one embodiment less than about 4 inches (about 10.2 cm) of tissue plus about 4 inches, and in another embodiment about 2 inches (about 5.1 cm) of air. Power and communications can be tailored to transmit over longer distances or can be tailored to have the remote transmitter 108 placed on the skin 124 adjacent to the high precision pump unit 106.

Further, the remote transmitter 108 can provide inductive power and telemetric control through a telemetric or transmission signal 122 to the high precision pump unit 106. The remote transmitter 108 may be configured to provide continuous power to the high precision pump unit 106. A dedicated microcontroller (or processor or microprocessor) within the remote transmitter 108 monitors the amount of power that is transmitted. Further still, a power management system may be implemented to optimize energy transmission between the remote transmitter 108 and the high precision pump unit 106 relative to their separation distance. For example, the power of the telemetric or transmission signals may automatically decrease as the remote transmitter 108 moves closer to the high precision pump unit 106, and may automatically increase as the remove transmitter 108 moves away from the high precision pump unit 106. This minimizes wasted energy, and minimizes energy exposure to the patient.

The systems and apparatus described herein use common surgical techniques to place the components in their respective positions within a patient. The surgical techniques may be identical or similar to those used in the placement of conventional gastric banding systems. For example, the gastric band 102 may be placed around the stoma using laparoscopic techniques, as known to those of skill in the art. Like a conventional access port, the high precision pump unit 106 may be sutured onto the rectus muscle sheath or any other conveniently accessible muscle. In order to achieve a secure attachment of the high precision pump unit 106, the unit may be sutured to the rectus muscle and remain securely attached for forces below about 6 lbf, and in one embodiment, below about 3 lbf (13.3 N). The tubing 110 from the high precision pump unit 106 passes through the rectus muscle into the peritoneal cavity in the same manner as the tubing of a conventional access port.

The systems and apparatus of the present invention further allow for a remotely controlled adjustment without needles, non-invasively, by using the remote transmitter 108. Also, should the remote transmitter 108 be unavailable, damaged, out of power, or in the event of an emergency, an adjustment of the gastric band 102 can be performed invasively using a needle. If any of the electronics associated with the systems and apparatus described herein become inoperable, the override port 212 can be used to add or remove fluid from the gastric band 102. The override port 212 and the hypodermic needle 112 can be used to adjust the gastric band 102.

Figure 2:
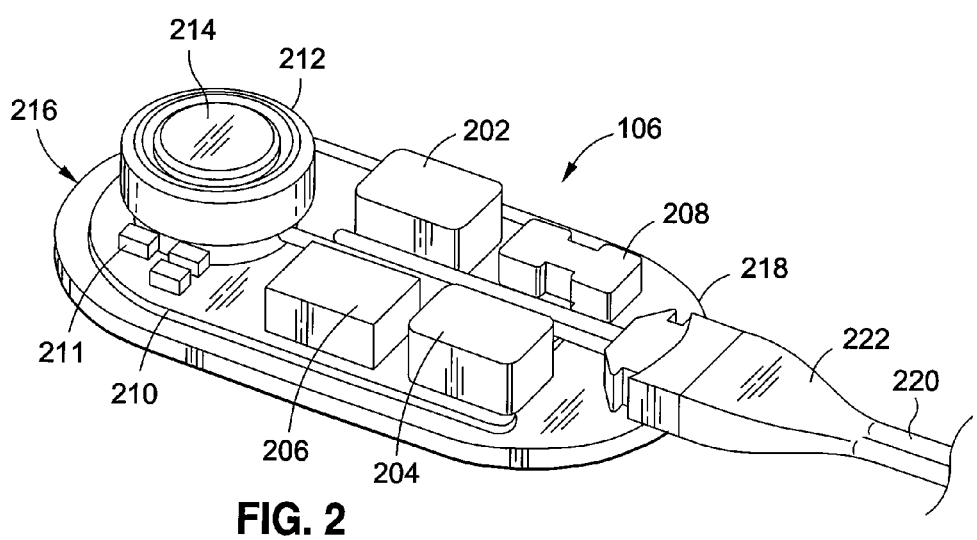
FIG. 2 illustrates an example configuration of the components of the high precision pump unit illustrated in FIG. 1 according to an embodiment of the present invention.

FIG. 2 illustrates the components of the high precision pump unit 106 of FIG. 1 according to an embodiment of the present invention. The components of the high precision pump unit 106 are positioned within an encasement or housing of the high precision pump unit 106. The housing of the high precision pump unit 106 has an internal volume of between about 0.75 in$^3$ to about 1.6 in$^3$. Exemplary internal features of the high precision pump unit 106 that fit within the encasement include a first valve 202, a second valve 204, a pump 206, a pressure/flow sensor 208, an electronics board 210 including an antenna 211, and the override port 212. The internal components of the high precision pump unit 106 can be arranged in any fashion appropriate for delivering and removing precise amounts of fluid from the gastric band 102 and the reservoir 104.

The pump 206 can be actively or passively driven. If the pump 206 is actively driven, a local power source such as a battery (not illustrated) is provided to drive the pump 206. If the pump 206 is passively driven, the pump 206 may be inductively powered by a device external to the high precision pump unit 106. In an exemplary configuration, the pump 206 is passively driven through inductive power received from the remote transmitter 108.

In various example embodiments, the pump 206 is an inductively powered, electrically driven, positive displacement piezoelectric pump, an electromechanical pump or a motor driven pump. The pump 206 provides a means to move the fluid into the gastric band 102.

The pump 206 can move fluid from the reservoir 104 into the gastric band 102 at rates higher than about 0.5 cc/min and higher than about 1.0 cc/min for band pressures less than about 20 psi (about 138 kPa) relative to the reservoir pressure. Alternatively, the fluid can be drained from the gastric band 102 to the reservoir 104 at rates higher than about 0.5 cc/min and higher than about 1 cc/min for band pressures above about 0.2 psi (about 1.38 kPa).

The first valve 202 and the second valve 204, illustrated in FIG. 2, can be any valve known in the art to allow precise delivery of fluid and precise flow rates therethrough. In one embodiment, the first valve 202 and the second valve 204 only allow fluid to move in one direction (i.e., are one-way valves), therefore, the two valves are situated in parallel with the high precision pump unit 106 allowing fluid to drain back from the gastric band 102. Further, the first valve 202 and the second valve 204 should have a precision orifice that restricts the flow rate to a well-characterized, precise amount.

The gastric banding system 100 may further comprise at least one flow or pressure sensor 208 disposed, for example, within the high precision pump unit 106. In an exemplary embodiment, two pressure sensors are situated within the fluid pathway between the first valve 202 and the second valve 204 and the gastric band 102. During a no-flow condition, both of the pressure sensors may be used to measure pressure thereby providing the benefits of redundancy and averaging.

For example, sensing or Measuring the pressure within the fluid pathway of the gastric banding system 100 provides diagnostic uses. Clinicians can measure pressure while a patient drinks water, recording and analyzing resulting pressure fluctuations which can help determine if the gastric band 102 is too restrictive. Whether the gastric band 102 is too restrictive can also be confirmed by the patient's response (generally discomfort) upon drinking the water, and can then be appropriately adjusted. Further, sensing or measuring pressure in the gastric banding system 100 can be useful in diagnosing system leaks or obstructions. For example, if the pressure consistently drops over an extended period of time, the clinician can diagnose a leak within the system 100 and plan for an appropriate treatment to fix the problem. In contrast, if there is an obstruction within the system 100 with a sustained pressure rise over time, the clinician can diagnose an obstruction within the system 100 and plan for an appropriate treatment to fix the problem.

The override port 212, illustrated in FIGS. 1 and 2, is an optional feature of some embodiments of the present invention. The override port 212 can be manufactured from a metal, in one embodiment, titanium or another non-radioopaque material and is accessible by insertion of a non-coring, hypodermic needle 112 (in FIG. 1) through a self-sealing septum 214 (in FIG. 2). The override port 212 allows a clinician to use the hypodermic needle 112 or a standard syringe to fill or drain the gastric band 102. Further, the override port 212 may be located on the distal end 216 of the high precision pump unit 106, for example, at a position substantially opposite from the proximal end 218 where the tubing 220 extends from the high precision pump unit 106. This placement of the override port 212 thereby reduces possible occurrences of a needle damaging the tubing 220. An extension body 222 emanating from the high precision pump unit 106 further protects the tubing 220 from accidental needle sticks.

The high precision pump unit 106 can be a passive device which may be entirely controlled and powered by the remote transmitter 108. The antenna 211 on the electronics board 210 is housed within the high precision pump unit 106. The remote transmitter 108 is coupled to the antenna 211 to allow the telemetric or transmission signals 122 of power to travel through the skin 124 (as illustrated in FIG. 1). The power issued or transmitted from the remote transmitter 108 is continually monitored by a dedicated microprocessor to ensure that the power transmission is minimized to the lowest level required for operation. To minimize the telemetric or transmission signals 122 of power and to optimize the signals 122 of command communication, the high precision pump unit 106 and the remote transmitter 108 have a channel frequency dedicated to command communication and a separate channel frequency dedicated to power transmission. The command communication can be configured, for example, to take place at about 402-406 MHz while the power transmission, for example, takes place at about 400 kHz. This command communication adheres to the frequency and power standards set by the Medical Implant Communications Service. To ensure accuracy, communication and control commands are verified by error check algorithms prior to data reporting or command implementation.

A portion of the electronics board 210 within the high precision pump unit 106 is devoted to conditioning and managing the power received at the antenna 211 or from a local battery. Communication electronics manage the bidirectional transmissions with timing verification and error checking. Controller circuits of the electronics board 210 send commands to the first valve 202, the second valve 204, the pump 206, and the pressure/flow sensor 208 and receive data back from the pressure/flow sensor 208. The electronics board 210 can be encased in a biocompatible sealant if further protection, or redundant protection, is necessary.

In one example embodiment, the systems and apparatus described herein are configured and structured to be compatible with MRI, or MRI safe, at, for example, 1.5 T. In the exemplary embodiment shown, the high precision pump unit 106 is entirely inductively powered. The systems utilize no permanent magnets, no long metallic wires or leads, and a minimal or negligible amount of ferrous or ferromagnetic material. The systems are substantially free or contain substantially no ferromagnetic materials. Substantially no ferromagnetic materials refers to materials containing less than about 5%, in one embodiment less than about 1% or 0.1% (w/w) of ferromagnetic material. The resulting systems are thus MRI safe given standard specifications regulating translational and rotational attraction, MRI heating, and imaging artifacts. In one embodiment, all materials selected for the systems are selected to be compatible and conditionally safe in an MRI environment.

Further, inductive powering of the high precision pump unit 106 causes energy or power to pass through bodily tissue. Since the bodily tissue absorbs a small amount of the energy passing through it, the heating of the tissue can be proportional to the total energy transferred. To ensure that the systems meet standards to minimize tissue heating (below 2° C. above body temperature per ISO 45652), the systems described herein have been designed to use very little power to move the fluid within the system and do not cause excessive heating of the patient's tissue.

The pressure/flow sensor 208 can monitor pressure inside the gastric band 102 as needed. Using the remote transmitter 108 to communicate with the high precision pump unit 106, a clinician can monitor pressure inside the gastric band 102, for example, in "real time" during an adjustment of the constriction within the gastric band 102. This will allow the clinician to observe the response of the gastric band 102 to a patient's adjustment. This may permit a new modality for the gastric band 102 adjustment management to monitor pressure as well as volume during an adjustment. With these new pressure sensing capabilities, the clinician can make a determination of whether there is a leak within the system (e.g., zero pressure reading) or whether there is an obstruction in the system (e.g., prolonged pressure rise).

In an example embodiment, the high precision pump unit 106 includes a first fluid line including a first pump for passing fluid in a first direction and a second fluid line in parallel with the first fluid line including a first valve and a second pump for passing fluid in an opposing direction. In another example embodiment, the second pump is not needed because the gastric band 102 provides enough pressure to move the fluid to the reservoir 104. The parallel line configuration allows for filling and draining of the gastric band 102 with a minimal number of components and minimal complexity.

The systems and apparatus described herein can achieve at least one of the following advantageous features. The total time required to complete a fill or drain of the gastric band 102 does not exceed about 10 minutes, and in one embodiment, about 5 minutes. The systems are able to adjust the volume in the gastric band 102 accurately to within about 0.1 cc or about 10%, whichever is greater. The pressure/flow sensor 208 has a resolution between about 0.010 psi to about 0.025 psi, and in one embodiment, about 0.019 psi (about 130 Pa). Better results than those stated above may also be achieved using the systems and apparatus described herein.

Components of the systems can be replaced without replacing the entire system and subjecting patients to overly invasive surgeries to replace entire systems when a single component is defective or damaged. For example, if the high precision pump unit 106 becomes damaged, it can be replaced independently of other components. Alternatively, if the gastric band 102 becomes damaged, it can be replaced independently of other components. The same is true of the tubing 110 and the reservoir 104. Although the components can be disconnected for single part replacement, the components shall not become dislodged from the tubing 110 for tubing pull-off forces less than about 10 lbf, and in one embodiment, less than about 5 lbf (22.2 N).

The systems described herein meet at least one safety specification. For example, in the event of any failure of the systems, either no change in the gastric band 102 tightness or a loosening of the gastric band 102 results. Further, the high precision pump unit 106 is biocompatible for long term implantation and the remote transmitter 108 is biocompatible for transient use both per ISO 10993. The systems are designed to have no significant interaction or interference with other electronics in any of the following modalities: implantable energy sources such as defibrillators and pacemakers; internal energy sources such as electrosurgical instruments; external energy sources such as ultrasound, x-rays and defibrillators; and radiofrequency signals such as pacemaker programmers and neurostimulators.

EXAMPLE 1

Implantation of a Gastric Banding System

A 40 year old female is diagnosed by her clinician as obese, weighing 510 lbs. The clinician suggests to the patient that she consider the gastric banding system 100 according to the present invention. She agrees and undergoes the implantation procedure. The gastric band 102 is implanted around her cardia thereby creating a stoma. The high precision pump unit 106 is sutured onto the rectus muscle sheath and the tubing 110 and the reservoir 104 passes through the rectus muscle into the peritoneal cavity and connects to the gastric band 102. The gastric banding system 100 comes pre-filled, so there is no need for the clinician to fill the gastric banding system 100 during the surgical procedure. The patient is sutured and sent to recovery.

EXAMPLE 2

Adjustment of a Gastric Banding System

The female patient of Example 1, after the completion of the surgical implantation, has her gastric band system 100 properly adjusted by her clinician. The clinician holds the remote transmitter 108 to the skin adjacent to the rectus muscle where the high precision pump unit 106 is located and initiates communication between the devices. An initial pressure of zero is displayed for the gastric band 102 as no fluid has been added to the gastric band 102. The clinician begins to fill the gastric band 102 using fluid (e.g., a saline solution or a biocompatible oil) housed within the reservoir 104 at a rate of about 1 cc/min and the entire filling takes less than about 5 minutes.

After filling, to about 20 psi, the patient drinks a glass of water in order to properly assess the proper inflation pressure of the gastric band 102 to ensure it has not been over inflated. Upon confirmation that the gastric band 102 is properly inflated, the procedure is completed and the patient returns to her normal life.

The patient instantly notices that she is less hungry than she previously had been and is consistently consuming less food as her appetite has been decreased. She returns to her clinician's office for a follow-up visit three months after her implantation and initial gastric band filling and she has lost about 20 pounds. A year later, she has lost nearly 60 lbs.

The gastric banding system 100 generally functions as follows. When a clinician uses the remote transmitter 108 to adjust the gastric band 102, the high precision pump unit 106 initiates a sequence of events to move a precise amount of fluid in the desired direction, where the filling is discussed in FIG. 3A and the draining is discussed in FIG. 3B.

Figure 3A:
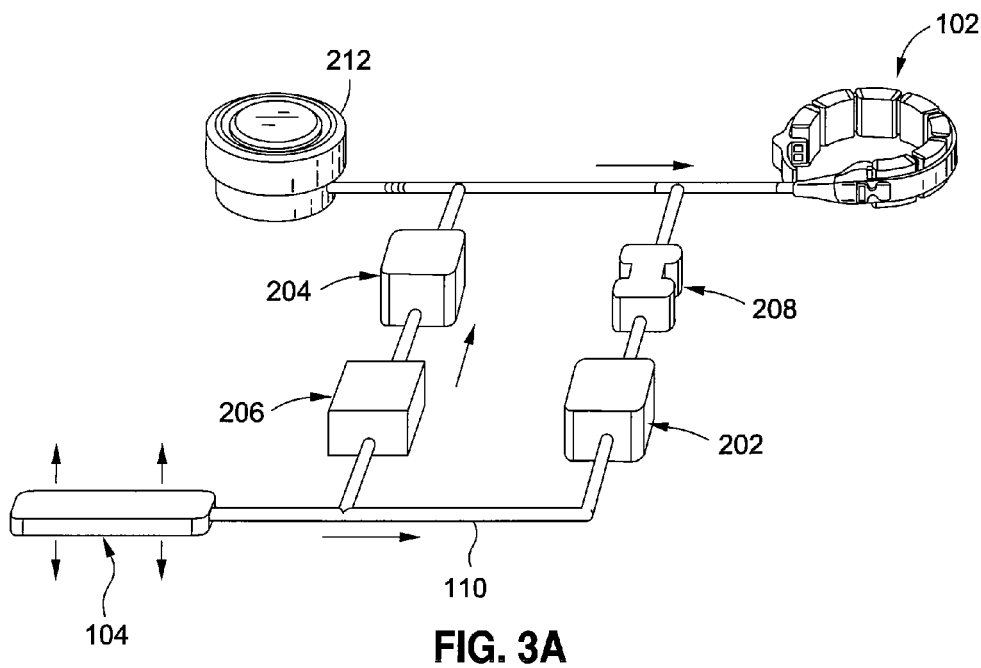
FIGS. 3A and 3B illustrate the filling and draining of a gastric band using the systems described herein according to an embodiment of the present invention.

FIG. 3A illustrates the filling of the gastric band 102. Just before pumping is initiated, the second valve 204, in line with the pump 206, is opened. The pump 206 creates a differential pressure to draw fluid out of the reservoir 104 and into the gastric band 102. The first valve 202 and the pressure/flow sensor 208 are not engaged. In one embodiment, the reservoir 104 is collapsible and does not impede the outward flow of fluid. Once the proper amount of fluid has been transferred from the reservoir 104 to the gastric band 102, the electronics board 210 shuts off the pump 206 and closes the second valve 204. The gastric band 102 now assumes the new higher pressure.

Figure 3B:
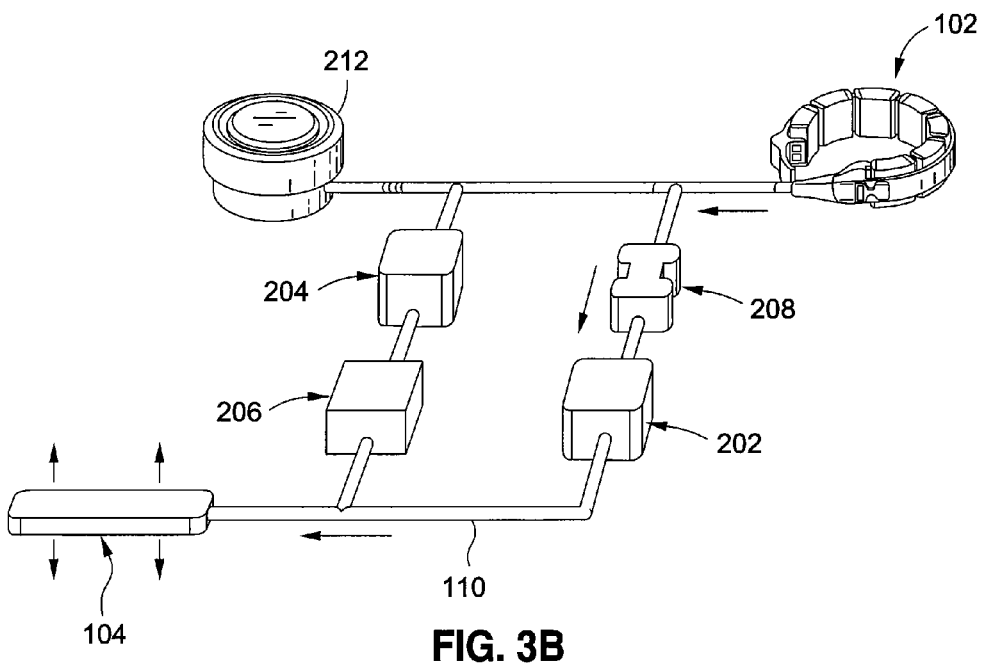

Referring to FIG. 3B, if the clinician decides to loosen the gastric band 102, fluid is released from the gastric band 102 and returned to the reservoir 104. Once the high precision pump unit 106 receives a drain command from the remote transmitter 108, the first valve 202 behind the pressure/flow sensor 208 opens. The amount of fluid released from the gastric band 102 can be monitored by the pressure/flow sensor 208. Once the correct volume of fluid has been transferred, the first valve 202 is closed. With both the first valve 202 and the second valve 204 closed, the fluid or volume in the gastric band 102 is maintained and the pressure in the gastric band 102 can be measured accurately.

When compared to conventional gastric banding systems having standard access ports which exclusively require syringe access (as opposed to being optional), the presently described systems and apparatus offer several advantages. First, the conventional access ports are located under a thick layer of fatty tissue, which is generally the case as the devices are generally used to treat obesity, and the access port can be difficult to locate. The present systems reduce or eliminate the need for (or to locate) the access port, as the use of the remote transmitter 108 removes the need for adjustment using the hypodermic needle 112.

Secondly, when accessing the access port in conventional systems, the ambiguity of its location may lead to damage by accidentally puncturing the tubing 110, which connects the access port to the gastric band 102. This can require a revision surgery in order to repair the punctured tubing. Further, when a conventional access port cannot be located by palpation, x-ray imaging may be required to guide a needle into the access port. Such imaging practices put a patient at risk for x-ray radiation exposure. The present systems and apparatus remove the need for these unnecessary procedures and save the patient from x-ray radiation exposure.

In the unlikely event that the override port 212 of the present invention is used, it may be located away from the tubing connection to the gastric band 102 to reduce the potential for tubing needle sticks. The high precision pump unit 106 has geometry and a rigid case that can be structured to facilitate the user in locating the override port 212 when needed.

Figure 4A:
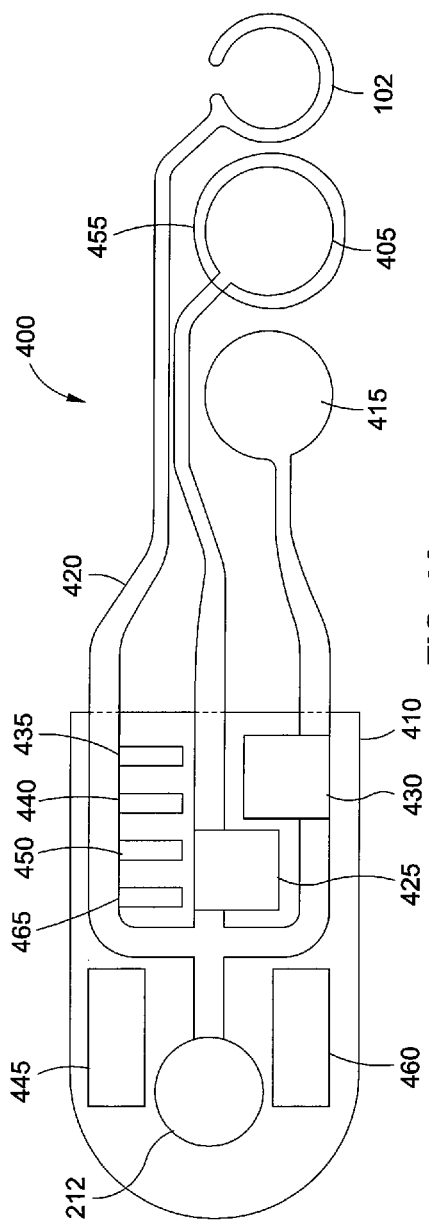
FIGS. 4A, 4B and 4C illustrate cross-sectional views of an implantable device that blocks fluid when a source valve is closed, uses potential energy to facilitate the movement of fluid when the source valve is open, and does not need a pump, according to an embodiment of the present invention.
Figure 4B:
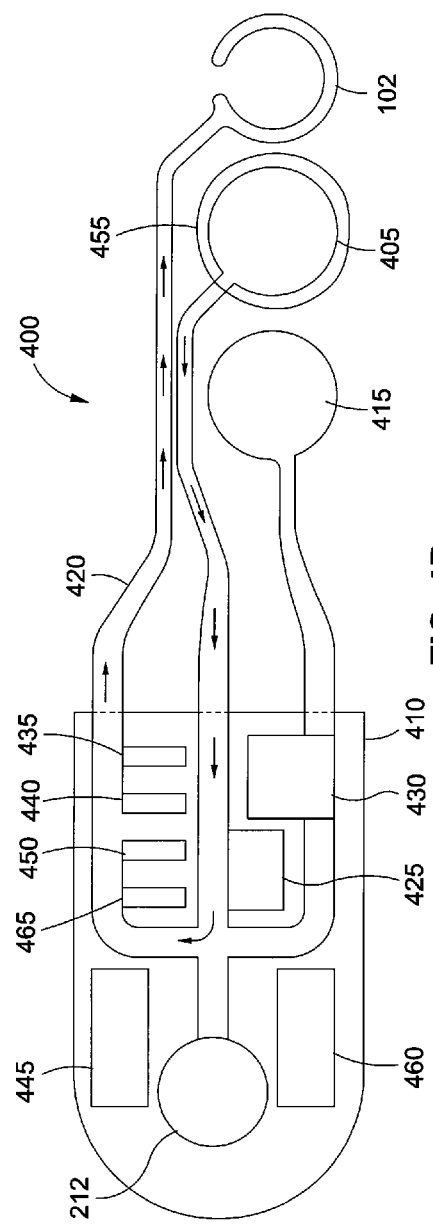
Figure 4C:
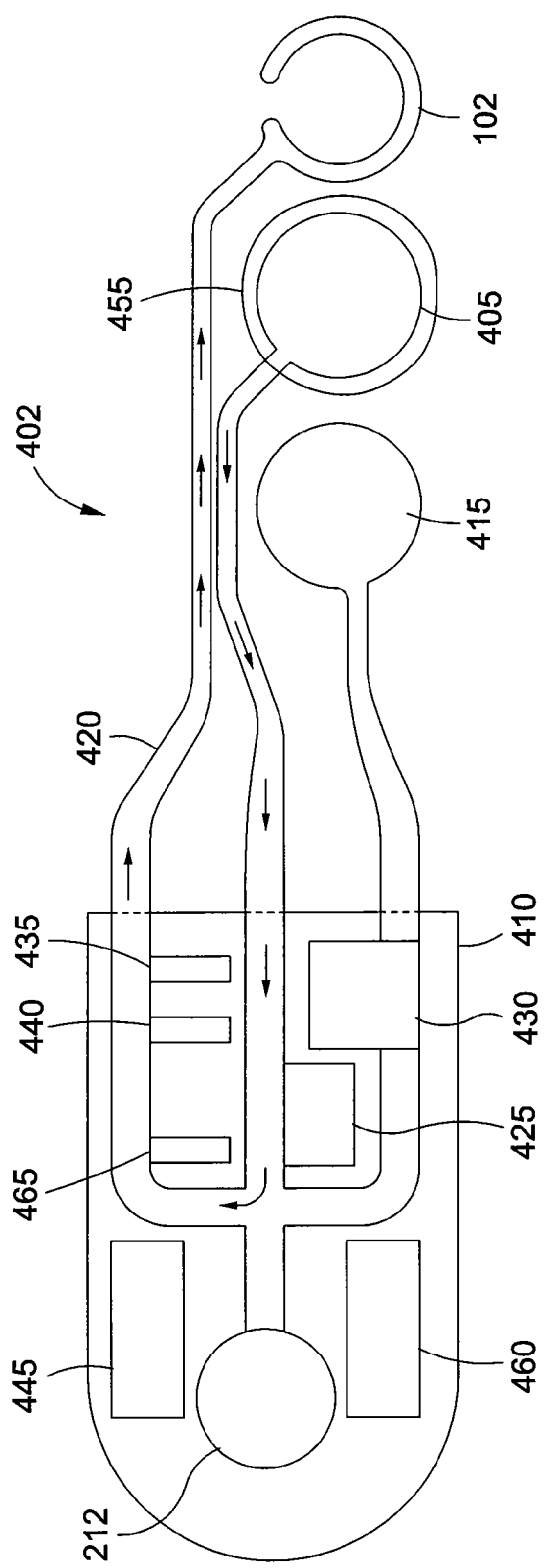

FIGS. 4A, 4B and 4C illustrate cross-sectional views of an implantable device 400 that blocks fluid when a source valve 425 is closed (FIG. 4A), and uses potential energy to facilitate the movement of fluid to the inflatable portion 114 of the gastric band 102 when the source valve 425 is open (FIG. 4B), and does not need a pump (FIG. 4C).

Referring to FIGS. 4A, 4B and 4C, the implantable device 400 can include a source reservoir 405, a gastric band 102, a drain reservoir 415, and a fluid control module 410. The tubing 420 (e.g., a hydraulic line) connects to the source reservoir 405, the drain reservoir 415, and the gastric band 102.

The term "potential energy," as used herein, represents various types of energy including elastic energy, elastic pressure, balloon energy, balloon pressure, pressurized energy, stored energy, tension, tensile pressure, inward stress from a stretched material, compressive force, mechanical force, and combinations thereof. As such, the implantable device 400 may be referred to as a balloon-based gastric band control system or a pressurized reservoir gastric band control system.

The terms energy and pressure are used herein. The potential energy is used to provide an inward pressure on the source reservoir 405 to move fluid out of the source reservoir 405.

The potential energy can be internal, external, or combinations thereof. The internal potential energy comes from the component itself. For example, the source reservoir 405 has an elastic shell, and the elastic shell can have an internal potential energy that creates an inward pressure, as oppose to a flaccid (e.g., limp) shell lacking internal potential energy. The external potential energy can come from an elastic band outside of the shell or other compression device, described further in FIG. 5.

The implantable device 400 includes the source reservoir 405. The source reservoir 405 is coupled to the gastric band 102. The source reservoir 405 has an elastic shell as part of the outside of the source reservoir 405. The elastic shell is configured to hold a fluid within the source reservoir 405.

The source reservoir 405 has a higher potential energy than the gastric band 102, at least initially, before the source reservoir 405 fills up the gastric band 102. The higher potential energy creates a higher inward pressure on the elastic shell of the source reservoir 405 to move the fluid from the source reservoir 405 to the inflatable portion 114 of the gastric band 102 when the source valve 425 and the gastric band valve 465 are open.

In one embodiment, the source reservoir 405 has a pressure between 10 and 50 psi. The pressure on the source reservoir 405 is greater than an atmospheric pressure (e.g., 0 psi).

The source reservoir 405 may be free floating within a cavity of the body, or may be sutured into place to prevent migration or hydraulic line kinking.

In one embodiment, the source reservoir 405 is an elastic capsule stretched like a filled balloon. In another embodiment, the source reservoir 405 is a container made of elastic, rubber, silicon, or combinations thereof. In another embodiment, the source reservoir 405 is a balloon.

The source reservoir 405 can be formed in any shape including an oblong, a sphere, a cone, a cube, a cylinder, a long tube and combinations thereof. The shape can be chosen to produce the desired pressure versus volume characteristics. The shape can be chosen to fit among the remaining components in the implantable device 400.

The materials for the source reservoir 405 can be anything used to build a balloon, such as an elastic polymer, rubber, non-rubber, silicon, non-silicon, and combinations thereof.

The source reservoir 405 can have a protective shell 455 surrounding and protecting the source reservoir 405. The protective shell 455 can be hard sided (e.g., rigid) and provide protection from puncturing and bursting. The protective shell 455 can be soft and flexible to minimize the size of the source reservoir 405. In one embodiment, the protective shell can be made of a biocompatible material.

The implantable device 400 may include the gastric band 102. The gastric band 102 is illustrated as being part of the implantable device 400. However, the gastric band 102 can also be separate from the implantable device 400.

The gastric band 102, described above in FIG. 1, has the inflatable portion 114 that receives the fluid from the source reservoir 405 and sends the fluid to the drain reservoir 415. In one embodiment, the gastric band 102 has an inner portion with a smooth surface touching the stomach. In another embodiment, the gastric band 102 has an inner portion with a non-smooth surface touching the stomach. The non-smooth surface includes textures and corrugated surfaces.

The implantable device 400 includes the drain reservoir 415. The drain reservoir 415 provides a location for disposal or storage of the fluid drained from the inflatable portion 114 of the gastric band 102 to reduce the size of the gastric band 102. The drain reservoir 415 may also store fluid for internally refilling the source reservoir 405.

The drain reservoir 415 can have a lower potential energy than the gastric band 102 (and the gastric band 102 can have a lower potential energy than the source reservoir 405). The lower potential energy of the drain reservoir 415 makes the inward pressure in the gastric band 102 higher than the inward pressure in the drain reservoir 415, causing fluid to flow from the gastric band 102 to the drain reservoir 415 when the drain valve 430 and the gastric band valve 465 are open.

Examples of a drain reservoir 415 include a retaining drain reservoir, a slow release drain reservoir, and a drain tube. The retaining drain reservoir stores the fluid without leaking, keeping the volume of fluid within the implantable device 400 constant (e.g., unchanged). The retaining drain reservoir itself typically has little or no potential energy, providing little or no pressure which would force fluid towards the gastric band 102 or the source valve 425. The retaining drain reservoir can be made of a flaccid material.

When using the retaining drain reservoir, the implantable device 400 can operate in a normal mode and in an internal refill mode. In the normal mode, the fluid travels from the source reservoir 405 to the gastric band 102 and from the gastric band 102 to the drain reservoir 415.

In the internal refill mode, the retaining drain reservoir, which does not leak, is used to refill (e.g., re-energized, recharge, etc.) the source reservoir 405. In the internal refill mode, the drain reservoir 415 refills the source reservoir 405 by opening both the source valve 425 and the drain valve 430, and closing the gastric band valve 465. The high potential energy of the source reservoir 405 can be overcome by electrical means, such as having a pump or an actuator connected to the drain reservoir 415 to refill the source reservoir 405 using an actuator (e.g., a pump).

For the internal refill mode, the drain reservoir 415 can have a volume that is at least as large as the volume of the gastric band 102 plus the volume of the source reservoir 405 to allow the drain reservoir enough space to store the fluid for the source reservoir 405 and to store the fluid from the gastric band 102.

The slow release drain reservoir is another embodiment for the drain reservoir 415. The slow release drain reservoir allows the fluid (e.g., an incompressible fluid, a saline solution, a sterile isotonic saline, etc.) to slowly exit into the body.

In one embodiment, the slow release reservoir includes a plurality of pore size holes. The holes are sized large enough to allow fluid to slowly pass through the slow release draining reservoir into the body of a human, but small enough to prevent the incursion of larger biological molecules and cells from the patient. In one embodiment, the slow release reservoir is comprised of an elastic material.

The slow release drain reservoir keeps the size of the drain reservoir 415 to a minimum, while fluid is harmlessly passed into the body. The fluid can be passed into the body at a controlled rate such that the fluid is not absorbed by the body. The fluid can be passed to the patient's peritoneal cavity.

The drain tube is another embodiment for the drain reservoir 415. The drain tube (e.g., the tube 420) does not store fluid. The drain tube releases the fluid directly into the body (e.g., the body cavity where the implantable device 400 is located) and may be thought of as not being a reservoir at all. However, the drain tube may also include a mechanism to prevent clogging of an exit (e.g., an exit hole or port) and prevent backflow into the drain tube. In one embodiment, a pressure relief valve can be the mechanism to prevent clogging and backflow. In another embodiment, a one-way valve is the mechanism. The clogging or backflow can be minimized by having the exit of the drain tube away from the gastric band 102 and the drain valve 430.

The drain tube is desirable because it occupies a smaller volume than the retaining drain reservoir and the slow release drain reservoir.

The drain reservoir 415 can be formed in any shape including an oblong, a sphere, a cone, a cube, a cylinder, a long tube and combinations thereof. The shape can be chosen to produce the desired pressure versus volume characteristics. The shape can be chosen to fit among the remaining components in the implantable device 400.

The materials for a drain reservoir 415 can be any material used to build a balloon, such as an elastic polymer, rubber, non-rubber, silicon, non-silicon, and combinations thereof.

The implantable device 400 also includes a fluid control module 410. The fluid control module 410 can include a source valve 425, a drain valve 430, a gastric band valve 465, the override port 212, a pressure sensor 435, a flow sensor 440, an actuator 450, an energy source 445, and controller electronics 460.

The fluid control module 410 may include the source valve 425. The source valve 425 is located between the source reservoir 405 and the gastric band 102. The source valve 425 does not contain any potential energy, and is opened and closed based on data from a telemetric signal received from the remote transmitter 108.

The fluid control module 410 may include the drain valve 430. The drain valve 430 is located between the gastric band 102 and the drain reservoir 415. The drain valve 430 is opened and closed based on data from a telemetric signal from the remote transmitter 108. The drain valve 430, when opened, allows fluid to flow from the inflatable portion 114 of the gastric band 102 to the drain reservoir 415.

The fluid control module 410 may include the gastric band valve 465. The gastric band valve 465 is located between the gastric band 102 and the override port 212. The gastric band valve 465 is opened and closed based on data from a telemetric signal from the remote transmitter 108. The gastric band valve 465 should be positioned to not block any fluid flow between the source reservoir 405 and the drain reservoir 430, and any fluid flow from the override port 212 to either the source reservoir 405 or the drain reservoir 430. In one embodiment, the gastric band valve 465 is positioned near the gastric band 102.

The gastric band valve 465 is a normally open valve, meaning it remains open except during the internal refill mode and during an external refill and draining mode.

The source valve 425, the drain valve 430, and the gastric band valve 465 can be any type of valve including an electrically operated valve, a piezoelectric valve, a solenoid valve, a passive valve, an active valve, and combinations thereof.

The fluid control module 410 may include the override port 212 that provides the external refill mode and an external drain mode. In the external refill mode, the hypodermic needle 112 is injected into the override port 212 to externally refill or drain the source reservoir 405, the drain reservoir 415, or the inflatable portion 114 of the gastric band 102.

As an example, to externally fill the source reservoir 405, fluid from the hypodermic needle 112 (e.g., a percutaneous needle, a syringe, an external source) can be injected into the override port 212, with the source valve 425 opened and the drain valve 430 and the gastric band valve 465 closed. The fluid from the hypodermic needle 112 can be injected into the source reservoir 405.

As an example, to externally drain the source reservoir 405, with the source valve 425 opened, and the drain valve 430 and gastric band valve 465 closed, the hypodermic needle 112, removes the fluid from the source reservoir 405 through the override port 212.

A similar external refilling and draining procedure can be performed on the drain reservoir 415 and the inflatable portion 114 of the gastric band 102, by having two valves open and one valve closed.

If the internal refill mode, the external refill mode, and the external drain mode are not desired, the gastric band valve 465 can be omitted.

The override port 212 is useful during emergency situations (e.g., draining the inflatable portion 114 of the gastric band 102), after a failure of a component of the implantable device, or at any desired frequency/schedule.

It may be useful to refill the source reservoir 405 when it is near empty. The term "near empty" can mean that the amount of fluid within the source reservoir 405 is not large enough for adjustments, and can mean the source reservoir 405 is not expanded enough to provide a desired potential energy (e.g., a potential energy greater than the gastric band 102).

The override port 212 can be used to remove fluid from the drain reservoir 415. This may be useful when the retaining drain reservoir is full. To minimize this occurrence, the retaining drain reservoir can be designed larger than the combined volume of both the source reservoir 405 and the inflatable portion 114 of the gastric band 102.

FIG. 4A illustrates the source valve 425 and the drain valve 430 being closed, with the gastric band valve 465 open. When the source valve 425 is closed, the fluid does not move from the source reservoir 405 and the gastric band 102.

FIG. 4B illustrates the source valve 425 and the gastric band valve 465 being open and the drain valve 430 being closed. When the source valve 425 is open, inward pressure causes the elastic shell of the source reservoir 405 to contract causing a portion of the fluid in the source reservoir 405 to move through the tubing 420 through the gastric band valve 465 and into the inflatable portion 114 of the gastric band 102. The source reservoir 405 can be under a higher pressure than the inflatable portion 114 of the gastric band 102 to facilitate movement of fluid. While filling the inflatable portion 114 of the gastric band 102, the drain valve 430 is kept closed to prevent the fluid from being pulled in two directions (e.g., trying to flow fluid up stream), which would require additional energy (such as a major external energy source) to move fluid to the inflatable portion 114 of the gastric band 102.

FIG. 4C illustrates an implantable device 402, similar to the implantable device 400, but without the actuator 450. The implantable device 402 advantageously does not need the actuator 450 because the potential energy is used to facilitate the movement of the fluid.

The fluid control module 410 may include the pressure sensor 435. The pressure sensor 435 is coupled (e.g., hydraulically connected, fluidically connected, mechanically connected, etc.) between the source valve 425 and the gastric band 102. The pressure sensor 435 is a way to control the volume of the fluid in the inflatable portion 114 of the gastric band 102 by determining and adjusting an amount of the fluid present in the inflatable portion 114 of the gastric band 102. In one embodiment, the pressure sensor 435 is used to measure the pressure within the inflatable portion 114 of the gastric band 102.

The pressure sensor 435 helps carefully control the volume of fluid within the inflatable portion 114 of the gastric band 102. Controlling the volume of fluid controls the size of the inner diameter of the gastric band 102 and the size of the inner diameter controls the size of the patient's stoma. When the stoma is of an appropriate size that is restricted by the gastric band 102, food held in the upper portion of the stomach provides a feeling of satiety or fullness that discourages overeating. Thus, the ability to control the stoma controls the effectiveness of the gastric band 102.

The pressure sensor 435 can control the volume of fluid in the inflatable portion 114 of the gastric band 102. For example, if a low pressure is measured (e.g., more fluid is needed in the inflatable portion 114 of the gastric band 102), the controller electronics 460 can open the source valve 425, with the drain valve 430 closed and the gastric band valve 465 open, to connect the source reservoir 405 to the gastric band 102. When a desired pressure is reached, the controller electronics 460 can close the source valve 425.

If a high pressure is measured (e.g., too much fluid is located in the inflatable portion 114 of the gastric band 102), the controller electronics 460 opens the drain valve 430, with the source valve 425 closed and the gastric band valve 465 open, to connect the drain reservoir 415 to the gastric band 102. In another embodiment, the pressure sensor 435 is used to monitor the internal pressure within the source reservoir 405.

The fluid control module 410 may also include the flow sensor 440. The flow sensor 440 is coupled between the source valve 425 and the gastric band 102. The flow sensor 440 may be used with the pressure sensor 435, or only the flow sensor 440 may be used to control the fluid in the inflatable portion 114 of the gastric band 102. The flow sensor 440 determines an amount of fluid present in the inflatable portion 114 of the gastric band 102 by measuring the flow of fluid and using those measurements to open and close the source valve 425 and the drain valve 430 to carefully control the volume of fluid in the inflatable portion 114 of the gastric band 102.

The fluid control module 410 may also include an actuator 450 coupled between the source valve 425 and the gastric band 102. The actuator 450 (e.g., an optional actuator, a pump, etc.) may be used to adjust the flow rate. The actuator 450 may be used to assist the potential energy of the source reservoir 405. The actuator 450 may pump fluid from the drain reservoir 415 to the source reservoir 405 during the internal refill mode.

The fluid control module 410 may include an energy source 445. The energy source 445 can power all of the electrical components of the fluid control module 410, including the source valve 425, the drain valve 430, the gastric band valve 465, the pressure sensor 435, the flow sensor 440, the actuator 450, and the controller electronics 460. For example, the energy source 445 can open and close the source valve 425.

The energy source 445 can provide the electrical energy to the implantable device 400 (e.g., using a battery). Additionally, the energy source 445 can provide energy coming from outside the implantable device 400 (e.g., inductive power from the remote transmitter 108).

The energy source 445, providing the electrical energy, is decoupled from (e.g., distinct and separate from) the potential energy of the source reservoir 405.

The fluid control module 410 may include controller electronics 460. The controller electronics 460 can be similar to the electronics board 210 discussed in relation to FIG. 2. For example, the controller electronics 460 can condition and manage the external energy (e.g., inductive power, radio-frequency power, etc.) received at the antenna 211 and the internal energy (e.g., a local battery). The controller electronics 460 can also send commands to components (e.g., the source valve 425, the drain valve 430, the flow sensor 440, the pressure sensor 445, etc.) and receive back data.

The fluid control module 410 is illustrated as being circular. However, the fluid control module 410 can be formed of any shape.

The implantable device 400 has several advantages, including not needing an actuator (e.g., a pump), not needing a major external energy source, using less electrical energy, and working with MRI scanning.

The implantable device advantageously does not need the actuator 450 because potential energy is used to facilitate the movement of fluid.

Additionally, the implantable device 400 does not need a major external energy source (e.g., a hypodermic needle pushing fluid into an access port) to move fluid into and out of the inflatable portion 114 of the gastric band 102, unlike conventional designs. Instead, a minor external energy source (e.g., the remote transmitter 108) can be used to remotely (e.g., telemetrically) open the source valve 425 and/or the drain valve 430).

Additionally, the implantable device 400 advantageously uses less electrical energy compared to conventional designs. For example, instead of using electrical energy (e.g., an electrically driven pump) to move fluid, potential energy is used. The implantable device 400 still can use electric energy, such as the energy source 445 for electrical energy (e.g., an internal battery, external inductive power, etc.), but less electrical energy is required due to the potential energy provided.

Lowering the electrical energy makes the implantable device 400 more energy efficient, reduces the patient's exposure to inductive power, reduces heating the patient's skin by not needing to use a large external energy source, reduces heating by not needing to use an internal electrical pump, and reduces safety problems by not needing to use a implantable energy source (e.g., a battery) because power can be provided externally.

Another advantage is that the source reservoir 405 does not require a long metal structure (e.g., spring) to create potential energy. By eliminating springs, this reduces the number of potentially failing parts and eliminates a part that can interact detrimentally with MRI scanning.

Figure 5:
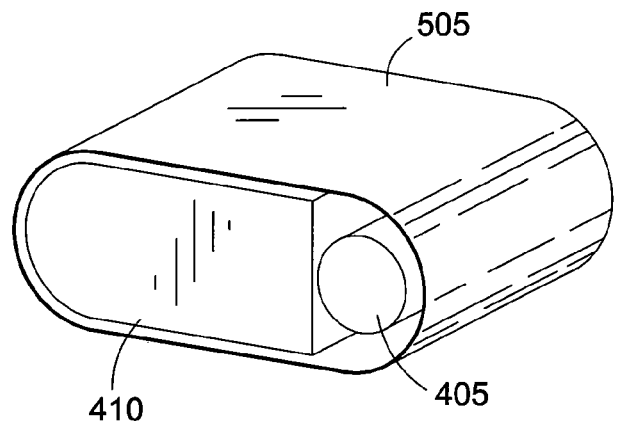
FIG. 5 illustrates a cross-section of an elastic band surrounding the fluid control module and the source reservoir of FIG. 4 according to an embodiment of the present invention.

Referring to FIG. 5, an elastic band 505 (e.g., an elastic net) surrounds the fluid control module 410 and the source reservoir 405. The elastic band 505 provides additional potential energy that applies additional inward pressure on the source reservoir 405. The elastic band 505 is useful when the source reservoir 405 has a low volume of fluid remaining. When the source reservoir 405 has a low volume of fluid remaining, the internal potential energy may be insufficient at that point. The elastic band 505 maintains a high potential energy even when a low fluid volume remains in the source reservoir 405.

Figure 6:
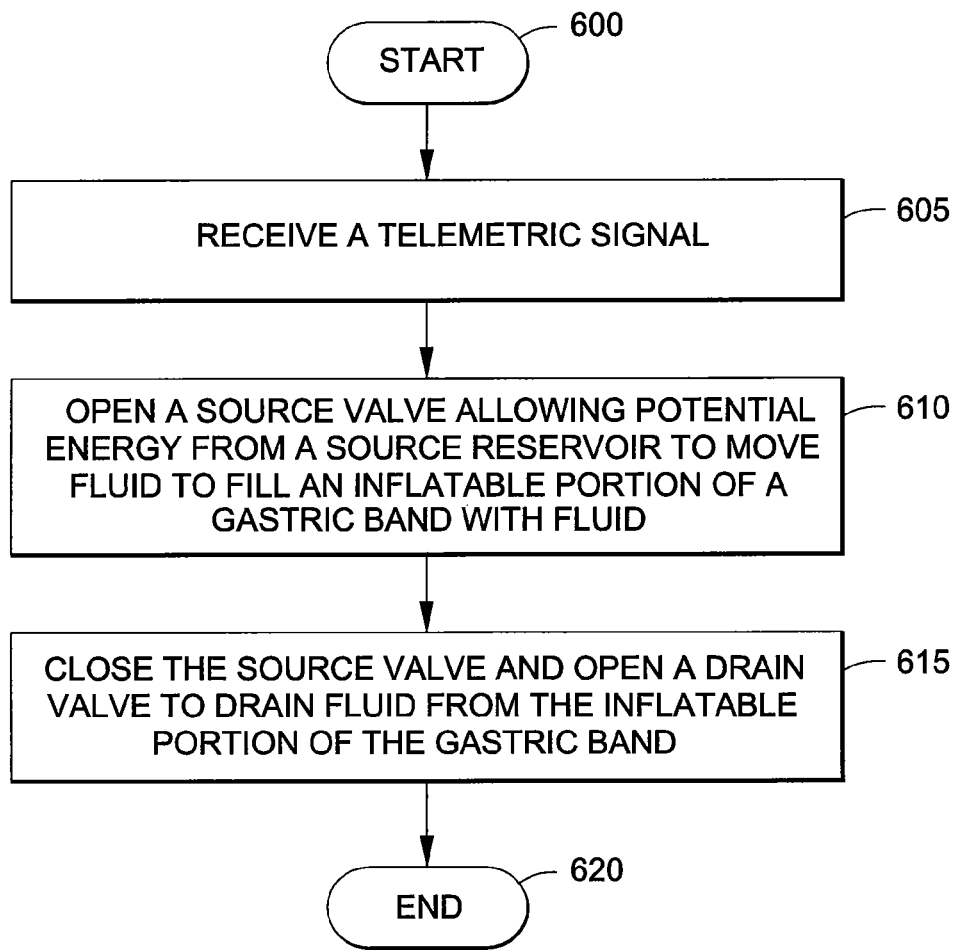
FIG. 6 is a flow chart of a method of moving fluid from the implantable device into the gastric band according to an embodiment of the present invention.

FIG. 6 is a flow chart of a method of using the implantable device 400 to control the movement of fluid between the source reservoir 405 and the inflatable portion 114 of the gastric band 102.

The process starts at step 600. At step 605, the implantable device 400 receives a telemetric signal from the remote transmitter 108. Next, the telemetric signal opens the source valve 425 allowing potential energy from the source reservoir 405 to move fluid to fill the inflatable portion 114 of the gastric band 102.

At step 615, the telemetric signal closes the source valve 425 and opens the drain valve 430 to drain fluid from the inflatable portion 114 of the gastric band 102 to the drain reservoir 415. The process ends at step 620.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable device that uses potential energy to facilitate the movement of fluid to an inflatable portion of a gastric band, the implantable device comprising:
a source reservoir configured for holding the fluid, the source reservoir having an elastic shell capable of contracting due to a first inward pressure;
a source valve configured to be coupled between the source reservoir and the gastric band, the source valve being open or closed based on a first telemetric signal received from a remote transmitter, and when the source valve is open, the first inward pressure causes the elastic shell to contract causing a portion of the fluid in the source reservoir to move into the inflatable portion of the gastric band, and when the source valve is closed, the fluid does not move outside the source reservoir;
a drain reservoir configured for storing the fluid and being coupled to the source reservoir such that a portion of the fluid is capable of moving from the drain reservoir to the source reservoir without moving through the inflatable portion of the gastric band when the source valve is open; and
an override port configured for filling or draining a portion of the fluid from the inflatable portion of the gastric band or the source reservoir or the drain reservoir, wherein the first telemetric signal is an electromagnetic signal.

2. The implantable device of claim 1 wherein the source reservoir is selected from a group consisting of an elastic polymer, a balloon, a rubber container, a non-rubber container, a silicon container, a non-silicon container, and combinations thereof.

3. The implantable device of claim 1 wherein the remote transmitter transmits the first telemetric signal to the source valve, the first telemetric signal having data to control the opening or closing of the source valve.

4. The implantable device of claim 1 wherein the drain reservoir is selected from a group consisting of an elastic polymer, a balloon, a rubber container, a non-rubber container, a silicon container, a non-silicon container, and combinations thereof.

5. The implantable device of claim 1 wherein the first inward pressure is greater than an atmospheric pressure.

6. The implantable device of claim 1 wherein the source valve is selected from a group consisting of an electrically operated valve, a piezoelectric valve, a solenoid valve, and combinations thereof.

7. The implantable device of claim 1 wherein the fluid is an incompressible fluid.

8. The implantable device of claim 7 wherein the incompressible fluid is a saline solution or a biocompatible oil.

9. The implantable device of claim 1, wherein the electromagnetic signal has at least one predetermined frequency.

10. The implantable device of claim 1, wherein the electromagnetic signal corresponds to at least one of a command communication signal and a power communication signal.

11. The implantable device of claim 10, wherein the command communication signal corresponds to a frequency of about 402 MHz to about 406 Mhz and the power communication signal corresponds to a frequency of about 400 MHz.

12. The implantable device of claim 1, wherein the electromagnetic signal includes a radio-frequency signal.

* * * * *